US011034632B2

(12) United States Patent
Schwint et al.

(10) Patent No.: US 11,034,632 B2
(45) Date of Patent: Jun. 15, 2021

(54) ETHANE RECOVERY PROCESS AND ALKYLATION PROCESS WITH ETHANE RECOVERY

(71) Applicant: Lummus Technology Inc., Bloomfield, NJ (US)

(72) Inventors: Kevin John Schwint, Long Valley, NJ (US); Sanjeev Ram, Berkeley Heights, NJ (US)

(73) Assignee: LUMMUS TECHNOLOGY LLC, Bloomfield, NJ (US)

( * ) Notice: Subject to any disclaimer, the term of this patent is extended or adjusted under 35 U.S.C. 154(b) by 0 days.

(21) Appl. No.: 15/266,398

(22) Filed: Sep. 15, 2016

(65) Prior Publication Data

US 2018/0072640 A1 Mar. 15, 2018

(51) Int. Cl.
| C07C 7/11 | (2006.01) |
| C07C 7/09 | (2006.01) |
| C07C 5/03 | (2006.01) |
| C07C 7/00 | (2006.01) |
| C07C 6/06 | (2006.01) |
| B01D 53/14 | (2006.01) |
| B01D 19/00 | (2006.01) |
| B01D 3/00 | (2006.01) |

(52) U.S. Cl.
CPC ............ *C07C 7/11* (2013.01); *B01D 3/009* (2013.01); *B01D 19/0068* (2013.01); *B01D 53/1418* (2013.01); *B01D 53/1487* (2013.01); *C07C 5/03* (2013.01); *C07C 6/06* (2013.01); *C07C 7/005* (2013.01); *C07C 7/09* (2013.01); *B01D 53/1406* (2013.01); *B01D 53/1493* (2013.01); *B01D 2252/20* (2013.01); *B01D 2252/205* (2013.01); *B01D 2256/245* (2013.01); *Y02P 30/40* (2015.11)

(58) Field of Classification Search
None
See application file for complete search history.

(56) References Cited

U.S. PATENT DOCUMENTS

| 3,200,164 A | 8/1965 | Gerald |
| 4,849,569 A | 7/1989 | Smith, Jr. |
| 5,003,119 A | 3/1991 | Sardina et al. |
| 5,243,115 A | 9/1993 | Smith, Jr. et al. |
| 5,453,559 A | 9/1995 | Phillips et al. |
| 7,071,369 B2 | 7/2006 | Pohl |
| 7,517,506 B2 | 4/2009 | Pohl |

(Continued)

FOREIGN PATENT DOCUMENTS

| WO | 2004076387 A2 | 9/2004 |
| WO | 2010042327 A1 | 4/2010 |

OTHER PUBLICATIONS

International Preliminary Report on Patentability and Written Opinion issued in corresponding International Application No. PCT/US2017/050700 dated Mar. 28, 2019 (17 pages).

(Continued)

*Primary Examiner* — Tam M Nguyen
(74) *Attorney, Agent, or Firm* — Osha Bergman Watanabe & Burton LLP

(57) ABSTRACT

Processes and systems for the production of ethylbenzene using a dilute ethylene feed and subsequent recovery of ethane in the alkylation vent gas.

14 Claims, 6 Drawing Sheets

(56) References Cited

U.S. PATENT DOCUMENTS

| | | | |
|---|---|---|---|
| 2010/0310431 A1* | 12/2010 | Schultz | C07C 2/66 422/144 |
| 2014/0124358 A1* | 5/2014 | Schwint | B01D 3/40 203/50 |
| 2016/0060189 A1* | 3/2016 | Sullivan | C07C 15/04 585/470 |
| 2018/0072640 A1* | 3/2018 | Schwint | C07C 7/09 |

OTHER PUBLICATIONS

Written Opinion issued in corresponding Singapore Applicaion No. 112019022915, dated Apr. 3, 2020 (7 pages).
Office Action issued in corresponding Indonesia Application No. PID201903017, dated Apr. 21, 2020 (4 pages with English Translation).

* cited by examiner

ETHANE RECOVERY PROCESS AND ALKYLATION PROCESS WITH ETHANE RECOVERY

FIELD OF THE DISCLOSURE

Embodiments disclosed herein relate generally to processes and systems for the extraction of ethane from a vapor stream. In other aspects, embodiments herein relate to processes and systems for the production of ethylbenzene using a dilute ethylene feed and subsequent recovery of ethane and unconverted ethylene contained in the alkylation vent gas.

BACKGROUND

Various processes for the production of alkylbenzene by the alkylation of benzene with an olefin are known in the art. Among the most common olefins used are ethylene and propylene. The alkylation of benzene with ethylene produces ethylbenzene. The alkylation of benzene with propylene produces cumene.

Ethylbenzene is an important chemical used mostly as a precursor for the production of styrene, which is subsequently polymerized to produce polystyrene. Various methods are known for the production of ethylbenzene. Typically, benzene and ethylene are combined in an alkylation reaction in the presence of a suitable catalyst. Various alkylation catalysts are known, and commonly used catalysts include Friedel-Crafts catalysts such as aluminum or boron halides, and various zeolites.

In addition to ethylbenzene, the reaction produces a byproduct containing poly-ethylated benzenes ("PEB") such as diethylbenzene, triethylbenzene and tetraethylbenzene. The poly-ethylated benzenes are undesirable and are usually recycled to a transalkylation reactor for conversion to ethylbenzene by reaction with benzene.

U.S. Pat. No. 5,003,119 discloses a liquid-phase process for the manufacture of alkylbenzenes, such as ethylbenzene and cumene, wherein a feed of fresh and recycle benzene and fresh olefin are reacted in the presence of an alkylation catalyst in a fixed-bed alkylator having at least two reaction stages wherein each stage is adiabatic. Essentially all of the olefin is completely reacted in each stage of the alkylator. Fresh olefin is fed into each stage of the alkylator.

Ethylbenzene and cumene have also been produced in a process wherein the alkylation reaction was performed by catalytic distillation (CD). The alkylation catalyst is contained in specially packaged bales, and the alkylation reaction is conducted in a mixed vapor-liquid phase reaction system, the CD alkylator. Such processes are disclosed in, for example, U.S. Pat. No. 5,243,115, among others. For polymer grade ethylene feedstock, with 99.9 vol. % or higher purity, over 99% of the ethylene can be easily converted in the CD alkylator.

The catalytic distillation process is particularly well suited for chemical grade ethylene feedstocks, typically containing 75 vol. % to 95 vol. % ethylene, and with the balance comprised of methane and ethane. With chemical grade ethylene, 95-99% of the ethylene conversion has been achieved in the CD alkylator. This level of conversion, however, requires a fairly large amount of baled catalyst.

Very dilute ethylene feedstocks, such as FCC offgas, can also be used with the catalytic distillation process. FCC offgas is typically composed of ethylene, methane and ethane, but also contains significant amounts of hydrogen and other light gases. With FCC offgas, only 75-80% of the ethylene conversion can be achieved in the CD alkylator. This low level of conversion also requires a very large amount of baled catalyst.

With the addition of a finishing reactor (a liquid phase reactor), the alkylator conversion can be relaxed to 75% to 80% of the ethylene feed in order to reduce the amount of baled catalyst in the CD alkylator. The liquid-phase fixed-bed finishing reactor fully reacts the unconverted ethylene. With chemical grade ethylene feedstock, the unreacted ethylene is condensed along with the rest of the CD alkylator overheads, and is reacted in the finishing reactor. With very dilute ethylene feedstocks, however, the ethylene must be absorbed into a circulating stream of benzene at high pressure.

Prior practice was to absorb the unreacted ethylene contained in the CD alkylator overhead and allow ethane to go together with the methane, hydrogen and other lights to a fuel gas header. The absorbed ethylene was then completely converted in the finishing reactor. Although some ethane and other gases were absorbed along with the ethylene, these gases built up in the solvent loop until they were eventually rejected in the absorber overhead. The ethane contained in the vent gas was ultimately lost, being sent to the fuel gas header. The absorber vent gas, for example, may be sent to a second vent absorber where the benzene is absorbed in a hydrocarbon stream (e.g., poly-ethylated benzenes) to minimize loss of aromatics.

U.S. Pat. Nos. 7,517,506 and 7,071,369 describe that it would be advantageous to have a substantially complete conversion of ethylene with a reduced overall amount of required catalyst, and disclose using an ethane stripper to improve the quality of the absorbent (lean oil). In these patents, the absorber overhead stream and stripper overhead stream were each mixed streams containing methane, hydrogen, lights, and ethane at different concentrations. These two overhead streams were combined, forming a further mixed stream, and sent to a fuel gas header, resulting in similar loss of the ethane.

SUMMARY OF THE CLAIMED EMBODIMENTS

Embodiments disclosed herein are directed toward the recovery of a high purity ethane stream from vent gases, such as ethane-containing vent gases from an alkylation system, among other ethane-containing vent gases. For example, embodiments disclosed herein may be used to recover a high purity ethane stream from an alkylation process using a dilute ethylene feed. The resulting high purity ethane stream may be used, for example, as a feed to an ethane cracker, resulting in additional higher-value ethylene.

In one aspect, embodiments disclosed herein relate to a process for the recovery of ethane. The process may include feeding a first stream comprising methane, ethane, and ethylene to a reboiled absorber column. The first stream may be contacted with an absorbent-reactant in the reboiled absorber column to absorb essentially all of the ethane and ethylene, producing a rich oil bottoms stream comprising the absorbent-reactant, ethylene, and ethane, and a vapor stream comprising methane. The ethylene and the absorbent-reactant may be reacted in a reaction zone, producing a reaction zone effluent comprising ethane and a reaction product. The effluent may then be separated in a stripper to produce a lean oil bottoms stream and an overhead vapor stream comprising ethane.

In another aspect, embodiments disclosed herein relate to a process for the recovery of ethane. The process may include feeding a first stream comprising methane, ethane, and ethylene to a reboiled absorber column. The first stream may be contacted with an absorbent-reactant in the reboiled absorber column, producing a rich oil stream comprising the absorbent-reactant, ethylene, and ethane, and a vapor stream comprising methane. The ethylene and the absorbent-reactant may be reacted in a reaction zone, producing an effluent comprising ethane and a reaction product, which may be stripped in a stripper to produce a lean oil bottoms stream and an overhead vapor stream comprising ethane. The overhead vapor stream may be contacted with a first portion of a second absorbent-reactant in a first scrubber to absorb unreacted ethylene or absorbent-reactant in the overhead vapor stream and to produce a first scrubber bottoms stream comprising the second absorbent-reactant and a first scrubber overhead stream comprising ethane. The vapor stream comprising methane may be contacted with a second portion of the second absorbent-reactant in a second scrubber to absorb ethane, ethylene, and/or absorbent-reactant present in the vapor stream and to produce a second scrubber bottoms stream comprising the second absorbent-reactant and a second scrubber overhead stream comprising methane.

In another aspect, embodiments disclosed herein relate to a process for the production of ethylbenzene. The process may include introducing benzene and an ethylene feed into an alkylation reaction zone in the presence of an alkylation catalyst to produce an alkylation effluent containing ethylbenzene and an alkylation overhead stream. The alkylation overhead stream may then be separated into a liquid portion containing benzene and a vapor portion containing unconverted ethylene, methane, and ethane. The unconverted olefin and the ethane in the vapor portion of the first alkylation overhead stream may be contacted with a lean oil containing benzene and alkylbenzene in an absorption zone to produce a rich oil stream containing the ethylene and the ethane and a vapor stream comprising the methane. The rich oil stream may be introduced into a second alkylation reaction zone containing a second alkylation catalyst to produce a first aromatic lean oil stream, which may be fractionated in a deethanizer to produce a deethanizer overhead vapor stream containing the ethane and a liquid bottoms stream containing the lean oil.

In another aspect, embodiments disclosed herein relate to a system for the recovery of ethylene from a dilute ethylene stream. The system may include a reboiled absorber column for contacting a stream comprising methane, ethane, and ethylene with an absorbent-reactant, producing a rich oil stream comprising the absorbent-reactant, ethylene, and ethane, and a vapor stream comprising methane. A reaction zone may be provided for reacting the ethylene and the absorbent-reactant, producing an effluent comprising ethane and a reaction product. A stripper is used for stripping the effluent to produce a lean oil bottoms stream and an overhead vapor stream comprising ethane. A first scrubber contacts the overhead vapor stream with a first portion of a second absorbent-reactant to absorb unreacted ethylene or absorbent-reactant in the overhead vapor stream and to produce a first scrubber bottoms stream comprising the second absorbent-reactant and a first scrubber overhead stream comprising ethane. A second scrubber contacts the vapor stream comprising methane with a second portion of the second absorbent-reactant to absorb ethane, ethylene, and/or absorbent-reactant present in the vapor stream and to produce a second scrubber bottoms stream comprising the second absorbent-reactant and a second scrubber overhead stream comprising methane.

In another aspect, embodiments disclosed herein relate to a system for the alkylation of benzene. The system may include an alkylation reaction zone, a separation zone, an absorption zone, a second alkylation reaction zone, and a deethanizer, among other components. The alkylation reaction zone may be used for reacting benzene with an ethylene feed in the presence of an alkylation catalyst to produce an alkylation effluent containing ethylbenzene and an alkylation overhead stream. The separation zone separates the alkylation overhead stream into a liquid portion containing benzene and a vapor portion containing unconverted ethylene, methane, and ethane. The absorption zone absorbs the unconverted olefin and the ethane in the vapor portion of the first alkylation overhead stream via contact with a lean oil containing benzene and alkylbenzene to produce a rich oil stream containing the ethylene and the ethane and a vapor stream comprising the methane. The second alkylation reaction zone is used for reacting benzene and ethylene in the rich oil stream to produce a first aromatic lean oil stream. The deethanizer fractionates the first aromatic lean oil stream to produce a deethanizer overhead vapor stream containing the ethane and a liquid bottoms stream containing the lean oil.

Other aspects and advantages will be apparent from the following description and the appended claims.

DETAILED DESCRIPTION

Figure 1:
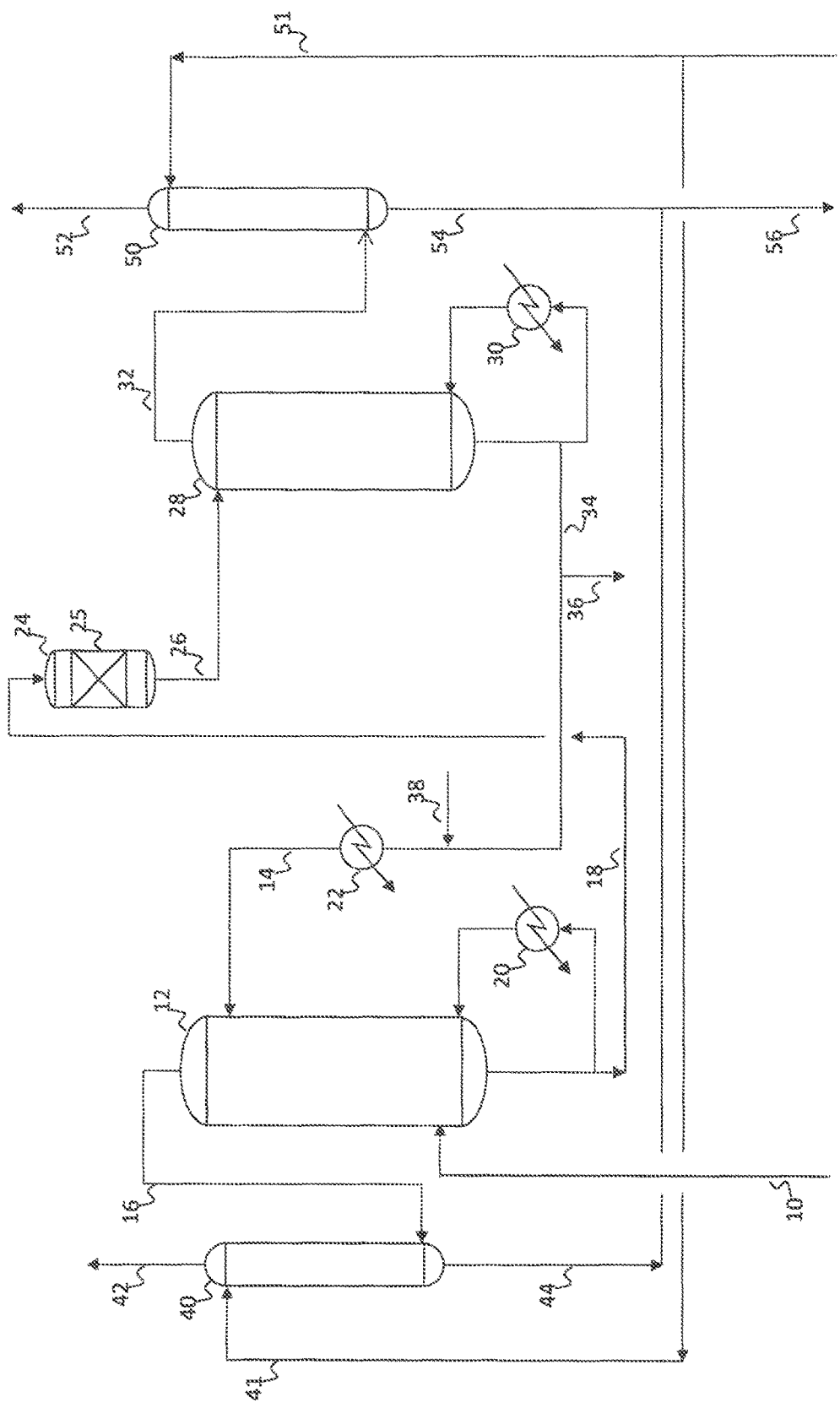
FIG. 1 is a simplified process flow diagram of a system for recovering ethane according to embodiments disclosed herein.

In one aspect, embodiments herein relate to processes and systems for the extraction of ethane from a vapor stream. In other aspects, embodiments herein relate to processes and systems for the production of ethylbenzene using a dilute ethylene feed and subsequent recovery of ethane in the alkylation vent gas.

Ethane and ethylene may be separated from methane, hydrogen, and/or other light gases according to embodiments herein via extractive distillation. Systems and processes disclosed herein may include, for example, a reboiled adsorber and stripper operating at conditions to adsorb ethane and ethylene from the vent gas, as opposed to losing the ethane to fuel gas. To efficiently achieve this objective, embodiments herein may also include a high degree of heat integration.

A dilute ethane- and ethylene-containing stream may be fed to separation systems according to embodiments herein for separation and recovery of the ethane. The dilute ethane- and ethylene-containing stream may be, for example, an offgas from a fluid catalytic cracker (FCC) offgas, residue fluid catalytic cracker (RFCC) offgas, and vacuum gas oil (VGO) cracking offgas, or may include a vent gas from an alkylation process using a dilute ethylene feed, or may be a combination of any of these streams. These offgas and vent gas dilute ethylene streams may contain from 0.1 wt % to 99+ wt % ethylene, for example, such as from about 5 wt %, 10 wt %, or 13 wt % to about 30 wt %. 40 wt %, or 50 wt % ethylene. The balance of the dilute ethylene stream may include, for example, hydrogen, methane, and ethane, and possibly some carbon monoxide, carbon dioxide, and/or nitrogen. For example, a typical FCC offgas may include 50 wt % to a 70 wt % methane and hydrogen, with the balance being about equal parts ethane and ethylene.

Separation systems according to embodiments herein may include a reboiled absorber column, a reaction zone, an ethane stripper, an ethane vent scrubber, and a lights vent scrubber. The ethane-containing stream may be fed to the reboiled absorber column, where it is contacted with an absorbent-reactant. The absorbent-reactant may be a hydrocarbon compound, such as benzene, suitable for the extraction of both ethane and ethylene from the ethane-containing stream, as well as for reaction with the ethylene in the alkylation reactor.

The reboiled absorber column may be used to absorb ethane and ethylene contained in the offgas or vent gas, producing a rich oil bottoms stream including the absorbent-reactant, ethylene, and ethane, and a vapor stream comprising methane and hydrogen. In some embodiments, essentially all of the ethane and ethylene present in the offgas or vent gas may be absorbed into the absorbent-reactant. To absorb essentially all of the ethane and ethylene, while rejecting a majority or essentially all of the methane and hydrogen, the reboiled absorber column may be operated with an overhead pressure in the range from about 200 psig to about 500 psig. For example, in the range from about 300 psig to about 450 psig. As another example, from about 350 psig to about 400 psig. This corresponds to a bottoms temperature in the range from about 150° C. to about 220° C., such as a temperature in the range from about 160° C. to about 210° C., or from a temperature in the range from about 170° C. to about 200° C., such as about 190° C., and with an overheads temperature in the range from about −20° C. to about 50° C., such as a temperature in the range from about −10° C. to about 30° C., such as a temperature in the range from about 0° C. to about 20° C., or from a temperature in the range from about 5° C. to about 150° C., such as about 10° C. Cold lean oil may be fed to the top of the reboiled absorber to improve separation efficiency.

The rich oil, including ethane, ethylene, and the absorbent-reactant, is then fed to the reaction zone, which may contain a suitable catalyst for a desired reaction between the ethylene and the absorbent-reactant. For example, the reaction zone may be an alkylation reaction zone containing an alkylation catalyst suitable for reacting ethylene with an absorbent-reactant, such as benzene. In some embodiments, the reaction zone may convert essentially all of the ethylene in the rich oil, producing a reaction zone effluent including ethane and a reaction product, such as ethylbenzene. Overall, the absorbent-reactant may be present at a ratio to ethylene of greater than stoichiometric. For example, benzene as an absorbent-reactant may be present at an absorbent-reactant to ethylene mole ratio in the range from about 2:1 to about 20:1. Where the reaction zone is an alkylation reaction zone for reacting benzene as the absorbent-reactant with ethylene, the alkylation reaction zone may be operated at temperatures in the range from about 180° C. to about 250° C. and pressures in the range from about 500 psig to about 1000 psig.

The effluent from the reaction zone may then be fed to the ethane stripper, where the effluent is separated to produce a lean oil bottoms stream, which may include both absorbent-reactant and the reaction product, and an overhead vapor stream comprising ethane. To achieve the desired separations in the ethane stripper, the ethane stripper column may be operated with an overhead pressure in the range from about 75 psig to about 500 psig. For example, from about 100 psig to about 450 psig. As another example, from about 150 psig to about 400 psig. As yet another example, from about 150 psig to about 200 psig. Although lower pressure would improve the separation efficiency of the ethane stripper, operating the ethane stripper at a higher pressure will allow for better heat integration with the reboiled absorber column and its reboilers, and therefore at a higher energy efficiency. Accordingly, the ethane stripper may be operated at a bottoms temperature in the range from about 200° C. to about 280° C., such as a temperature in the range from about 220° C. to about 270° C., or from a temperature in the range from about 230° C. to about 260° C., such as about 250° C., and with an overheads temperature in the range from about 165° C. to about 245° C., such as a temperature in the range from about 185° C. to about 235° C., or from a temperature in the range from about 195° C. to about 225° C., such as about 215° C. Following stripping, at least a portion of the lean oil bottoms stream, which may include both reaction product and absorbent-reactant, is purged from the circulating solvent loop to remove the net products of reaction, and the remainder of the lean bottoms stream is recycled to the reboiled absorber column as the absorbent-reactant.

As noted above, the absorbent-reactant is withdrawn from the ethane stripper at a temperature of greater than 200° C., for example, and is introduced to the reboiled absorber column, such as proximate an upper end of the reboiled absorber column, at a temperature of less than about 50° C., for example. The heat contained within the lean oil bottoms stream recovered from the ethane stripper may be recovered, enhancing the energy efficiency and cost-effectiveness of the overall process. In some embodiments, for example, the reboiled absorber column may include multiple reboilers configured to sequentially extract heat from the lean oil bottoms stream from the ethane stripper. In some embodiments, the multiple reboilers may include one or more side reboilers. Additionally or alternatively, the ethane stripper may include one or more stripper side reboilers for extracting heat from the lean oil bottoms stream from the stripper via one or more stripper side reboilers. Additional heat integration may be achieved by contacting the lean oil bottoms stream in indirect heat exchange with the reaction zone effluent and/or the rich oil bottoms stream.

The lean oil stream, as noted above, may include a desired reaction product as well as absorbent-reactant. A portion of the lean oil stream may be recycled to the reboiled absorber column, and a portion of the lean oil stream may be withdrawn from the separation system as a product stream. Fresh and/or make-up adsorbent-reactant may be admixed with the remaining portion of the lean oil stream. The withdrawal of product and addition of adsorbent-reactant may allow for control of the ethylene to absorbent-reactant mole ratio.

The overhead vapor recovered from the ethane stripper may include essentially no ethylene, as consumed in the reaction zone, as well as little or none of methane, hydrogen, and other light gases that may have been contained in the vent gas or offgas. This overhead vapor stream, being primarily ethane, may then be used as a feedstock, such as to an ethane cracker.

Operating conditions in the reboiled absorber column and in the ethane stripper may be such that a portion of the absorbent-reactant and/or reaction product is carried out with the respective overhead vapor streams. The vapor stream recovered from the reboiled absorber column may be fed to a lights vent scrubber, and the overhead vapor stream recovered from the ethane stripper may be fed to an ethane vent scrubber. In each scrubber, the respective vapor fractions may be contacted with a second absorbent-reactant to absorb any absorbent-reactant in the overhead vapor streams.

For example, in some embodiments the absorbent-reactant is benzene, as noted above, and the second absorbent-reactant may be poly-ethylated benzene (PEB). The overhead vapor stream from the ethane stripper may be contacted with a first portion of the second absorbent-reactant in a first scrubber to absorb absorbent-reactant contained in the overhead vapor stream and to produce a first scrubber bottoms stream including the second absorbent-reactant and a first scrubber overhead stream comprising ethane. The overhead vapor stream from the reboiled adsorber column may be contacted with a second portion of the second absorbent-reactant in a second scrubber to absorb absorbent-reactant present in the vapor stream and to produce a second scrubber bottoms stream including the second absorbent-reactant and a second scrubber overhead stream comprising methane. Where the absorbent-reactant is benzene, and the second absorbent-reactant comprises poly-ethylated benzenes, the resulting bottoms streams may be combined and reacted, such as in a transalkylation reaction zone, to produce additional reaction product, ethylbenzene.

As described above, separation systems disclosed herein may include a reboiled adsorber column to absorb both ethylene and ethane away from methane and hydrogen, and a reaction zone to produce a reaction product of the adsorbent-reactant and the adsorbed ethylene, thus facilitating separation of the ethane from ethylene and producing a desired reaction product. Separation systems according to embodiments herein may be used, for example, in a process for the production of ethylbenzene (adsorbent-reactant=benzene, target reaction product=ethylbenzene, and second adsorbent-reactant=poly-ethylated benzene).

A process for the production of ethylbenzene according to embodiments herein may include introducing benzene and an ethylene feed into an alkylation reaction zone containing an alkylation catalyst. In the alkylation reaction zone, the benzene and ethylene may be contacted with the catalyst, producing an alkylation effluent containing ethylbenzene. The alkylation reaction zone may be a liquid-phase alkylation reactor in some embodiments, where the effluent may be fed to a flash drum to separate the liquid products, ethylbenzene and unreacted benzene, from a vapor product, which may include benzene and unreacted ethylene, for example. In other embodiments, the alkylation reaction zone may be a catalytic distillation reactor system, producing a bottoms product containing the ethylbenzene and an alkylation overhead stream, which may include unreacted ethylene. Where a dilute ethylene stream is used as a feedstock, the overhead stream from the catalytic distillation reactor system may include unreacted ethylene, ethane, methane, and hydrogen, among other components.

The vapor stream, such as the overhead vapor stream from the catalytic distillation alkylator, may be cooled and partially condensed, separating the alkylation overhead stream into a liquid portion containing benzene and a vapor portion containing unconverted ethylene, ethane, methane and hydrogen. The vapor portion, a vent gas from the alkylation reaction system, may then be fed to a separation system, such as described above. In the separation system, the unconverted olefin and the ethane in the vapor portion of the alkylation overhead stream may be separated from the methane, hydrogen, and other light gases present via contact with a lean oil containing benzene and alkylbenzene in a reboiled absorption zone, producing a rich oil stream containing the ethylene and the ethane and a vapor stream comprising the methane and hydrogen. The absorption zone may be operated, for example, at conditions of temperature and pressure to absorb essentially all of the ethylene and ethane into the rich oil stream. The rich oil stream may then be introduced into a second alkylation reaction zone (a finishing reactor) containing a second alkylation catalyst, reacting the benzene and ethylene to produce a first aromatic lean oil stream. The lean oil stream may then be fed to an ethane stripper (deethanizer), fractionating the first aromatic lean oil stream to produce a deethanizer overhead vapor stream containing the ethane and a liquid bottoms stream containing the lean oil.

The deethanizer overhead vapor stream may be contacted with a first portion of a second absorbent including poly-ethylated benzene in a first scrubber to absorb benzene in the deethanizer overhead vapor stream and to produce a first scrubber bottoms stream, including benzene and poly-ethylated benzene, and a first scrubber overhead stream, including the ethane. The vapor stream from the reboiled absorption zone may be contacted with a second portion of the second absorbent in a second scrubber to absorb benzene present in the vapor stream and to produce a second scrubber bottoms stream and a second scrubber overhead stream comprising methane, hydrogen and other light components. The first scrubber bottoms steam and the second scrubber bottoms stream may be combined and fed to a transalkylation reaction zone, where the poly-ethylated benzene and benzene may be reacted in the presence of a transalkylation catalyst to convert at least a portion of the poly-ethylated benzene and benzene to ethylbenzene. The effluent from the transalkylation reaction zone may then be recycled to the catalytic distillation reactor system for continued separation and reaction of the various components.

Embodiments disclosed herein thus utilize extractive distillation and reaction to separate ethane from ethylene, methane, hydrogen and other light components. Reboiled vent absorbers according to embodiments herein may have multiple reboilers to put heat into the bottom of the absorber column in order to strip out dissolved methane, hydrogen and other light components. This heat input may increase the need for lean solvent (adsorbent-reactant) fed to the top of the absorber in order to ensure all ethane is absorbed into the rich solvent. The combination of higher solvent rate and reboiler heat input may result in the efficient and essentially complete separation of ethane from methane, hydrogen and other lights. Therefore, the light key is methane and the heavy key is ethane.

Embodiments herein may have a unique design for heat integration to recover and re-use most of the process heat. The lean solvent is heated, for example, from 10° C. at the top of the reboiled absorber column to approximately 190° C. at the bottom of the reboiled absorber column. The rich solvent leaving the bottom of the absorber is heated further to approximately 250° C., for example, at the bottom of the ethane stripper. The lean solvent from the bottom of the ethane stripper is then cooled back down to 10° C. before re-entering the top of the absorber. A very high degree of heat interchange is required to achieve an acceptable level of heat efficiency and to minimize heat lost to cooling water.

Embodiments herein may include a special reboiler arrangement at the bottom of the absorber to allow light components to be stripped from the rich solvent, leaving only the net feed of ethane in the bottoms. Embodiments herein may also include a special reboiler arrangement at the top and side of the ethane stripper to efficiently strip ethane from the rich solvent. This also serves to straighten (keep more constant) the vapor traffic in the stripper.

Separation systems disclosed herein may allow the elimination of the usual alkylator vent condenser on the alkylator overhead drum in order to provide more heat to the bottom of the absorber column. Additionally, embodiments herein may takes the finishing reactor loop blowdown from the lean solvent after the maximum amount of heat has been recovered from this stream. The blowdown is sent to the alkylator overhead drum as make-up benzene for the catalytic distillation alkylation system. Fresh benzene may be added just downstream of the blowdown takeoff as make-up benzene to the finishing reactor loop.

Referring now to FIG. 1, a simplified process flow diagram of a system for separating ethane from ethylene and methane according to embodiments herein is illustrated. A feed stream 10 containing methane, ethane, and ethylene, such as a vent gas from an alkylation process using a dilute ethylene feedstock, may be fed to a reboiled vent absorber 12. In the reboiled vent absorber 12, the vent gas may be contacted in countercurrent flow with an adsorbent-reactant, such as benzene, fed via flow line 14. Operating conditions in the reboiled vent absorber 12 may be such that essentially all of the ethane and ethylene are absorbed into the absorbent-reactant benzene, resulting in an overhead stream 16, which may include the methane and possibly some entrained benzene, and a bottoms stream 18, which may include the ethane, ethylene, and the adsorbent-reactant. To achieve the desired separation of methane and adsorption of ethane and ethylene, one or more reboilers 20, which may include one or more side reboilers (not illustrated), and one or more feed coolers 22 may be used to provide a desired temperature differential between the overheads 16 and bottoms 18.

Bottoms stream 18, which includes ethane, ethylene, and adsorbent-reactant, may then be fed to a reaction zone 24. Reaction zone 24 may include a catalyst 25 suitable for the desired reaction between adsorbent-reactant and ethylene, and may be operated under conditions to convert essentially all of the ethylene, producing a reaction effluent 26 containing unreacted adsorbent-reactant, ethane, and a desired reaction product, such as ethylbenzene (e.g., ethylene+benzene→ethylbenzene over an alkylation catalyst).

The reaction zone effluent 26 may then be fed to an ethane stripper (deethanizer) 28 for separation of the adsorbent-reactant and reaction product from the ethane. Ethane stripper 28 may include one or more reboilers 30, which may include one or more side reboilers (not shown) to provide the necessary temperature differential to recover an overheads stream 32, which may be primarily ethane with entrained adsorbent-reactant and reaction product, and a bottoms stream 34 which contains no or essentially no ethane. A portion of the bottoms stream 34 may be recycled to reboiled vent absorber 12 as the adsorbent-reactant 14, and a remaining portion of the bottoms stream 34 may be recovered via flow line 36, providing for recovery of the reaction product and limiting buildup of the reaction product within the separation system. Fresh or make-up adsorbent-reactant may be fed introduced to the system via flow line 38.

Overheads stream 16, including methane and any entrained adsorbent-reactant, may be fed to a methane scrubber 40 to separate the methane from any entrained adsorbent-reactant. In methane scrubber 40, the overhead vapors may be contacted in countercurrent flow with a second adsorbent 41, or a second adsorbent-reactant, producing an overheads stream 42, including the methane, and a bottoms stream 44, which may include the second adsorbent and any entrained adsorbent-reactant.

Overheads stream 32, including ethane and any entrained adsorbent-reactant, may be fed to an ethane scrubber 50 to separate the ethane from any entrained adsorbent-reactant. In ethane scrubber 50, the overhead vapors may be contacted in countercurrent flow with the second adsorbent 51, or the second adsorbent-reactant, producing an overheads stream 52, including the ethane, and a bottoms stream 54, which may include the second adsorbent and any entrained adsorbent-reactant. Bottoms streams 44, 54 may be combined and recovered via flow line 56.

Figure 2:
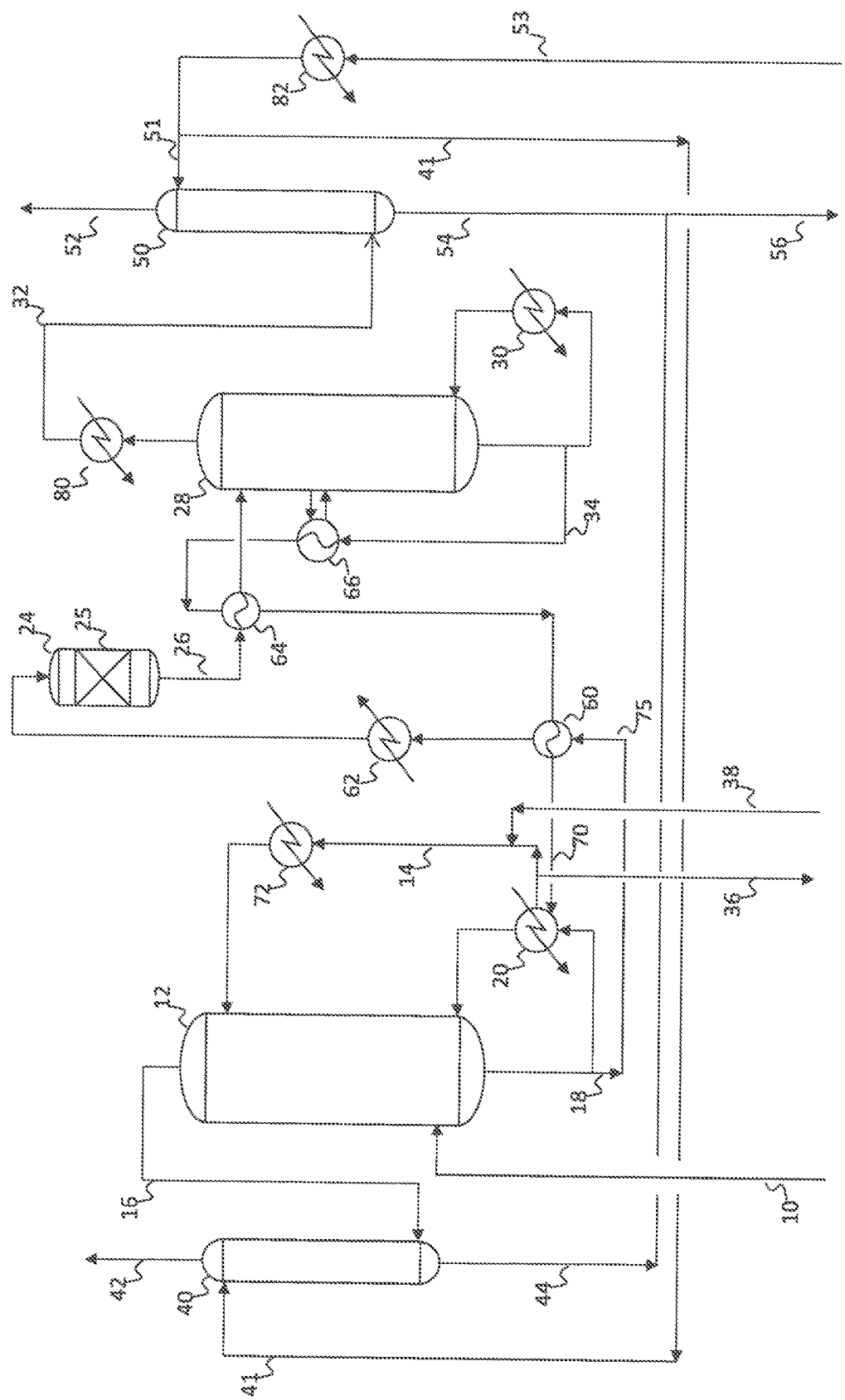
FIG. 2 is a simplified process flow diagram of a system for recovering ethane according to embodiments disclosed herein.
Figure 3:
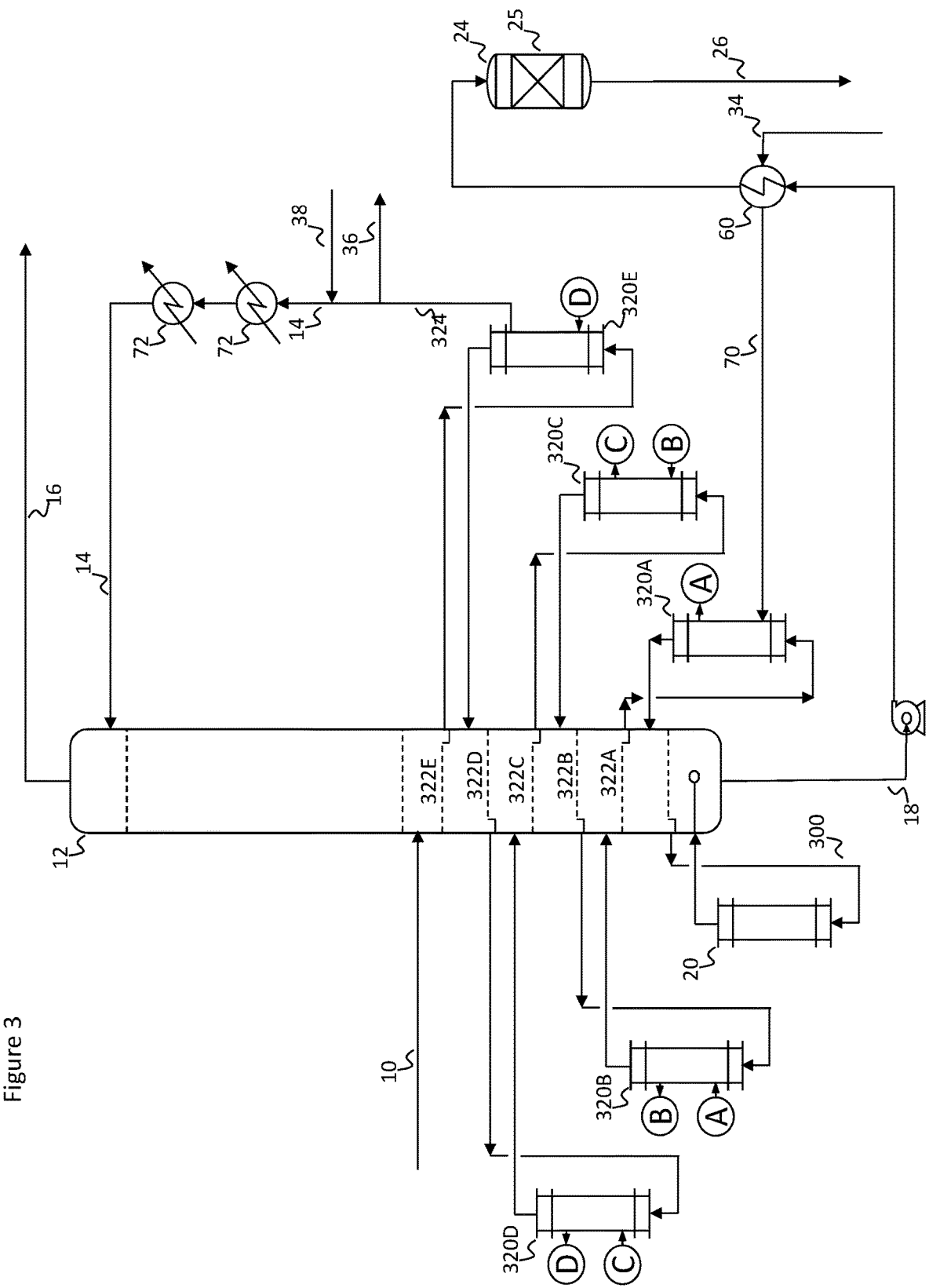
FIG. 3 is a simplified process flow diagram of a reboiled absorber column according to embodiments herein.
Figure 4:
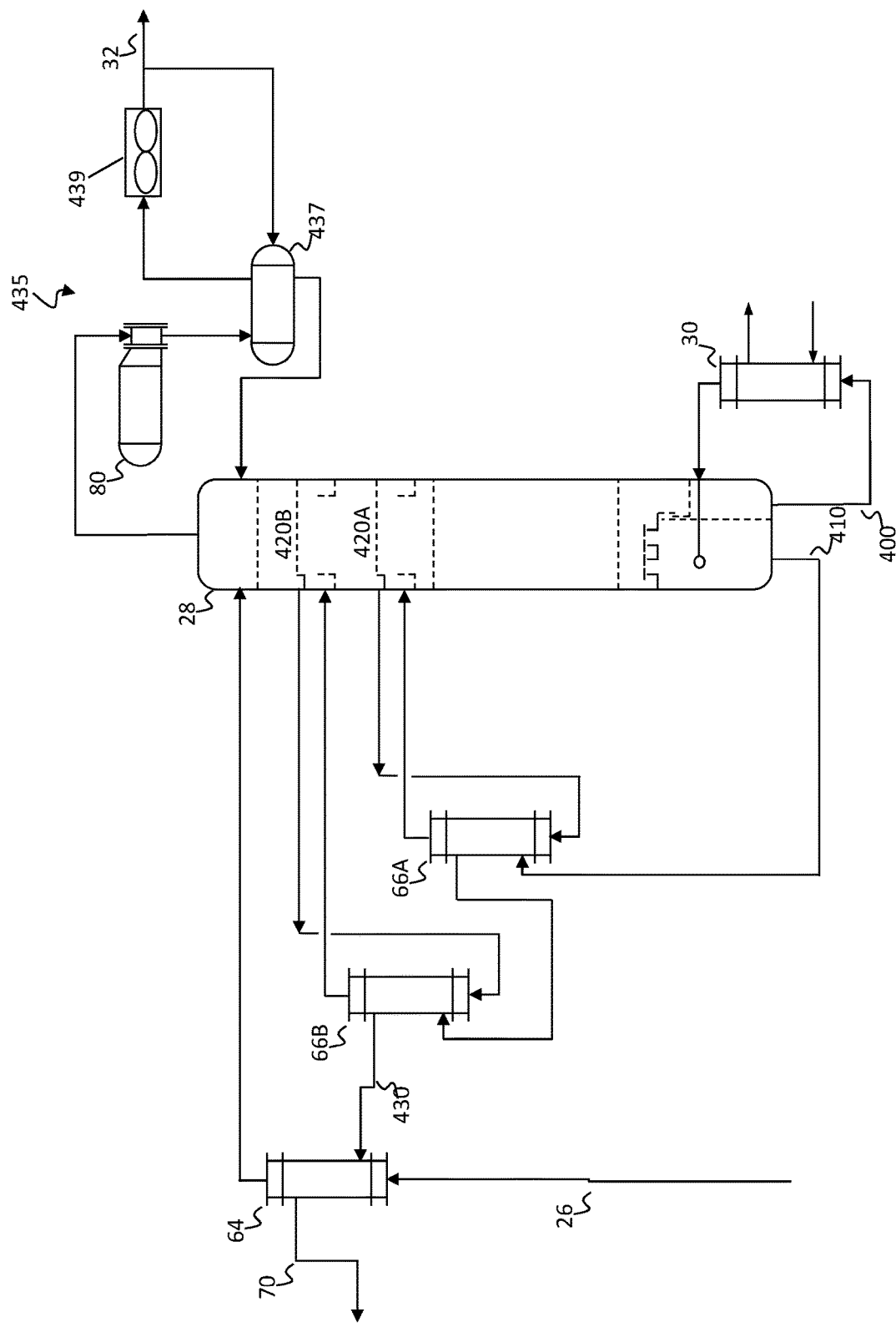
FIG. 4 is a simplified process flow diagram of a reboiled ethane stripper according to embodiments herein.

The efficiency of embodiments of the processes and systems for ethane recovery may be enhanced, as noted above, via use of a high degree of heat integration, such as illustrated in FIG. 2-4, where like numerals represent like parts.

Referring now to FIG. 2, the general flow scheme of the separation system is as described with respect to FIG. 1. As illustrated in FIG. 2, heat integration may include one or more of the following.

Reboiled absorber column 12 bottoms stream 18, which may be at a temperature of about 190° C., for example, may be heated via indirect heat exchange with the ethane stripper bottoms 34 in cross exchanger 60. The bottoms stream 18 may be further heated to reaction zone 24 operating conditions via exchanger 62.

Reaction zone 24 effluent 26, which may be at a temperature of about 200° C., for example, may be heated via indirect heat exchange with ethane stripper bottoms 34 in cross exchanger 64 prior to introduction into ethane stripper 28. Ethane stripper 28, as noted above, may be operated at a bottoms temperature of about 250° C., for example, and may include a reboiler 30 and may also include one or more side reboilers 66 as further illustrated in FIG. 4, described below. Side reboilers 66 may be used to provide additional heat to stripper 28. In some embodiments, as illustrated in FIG. 2, the side reboilers 66 may be used to recover heat from stripper bottoms stream 34.

Following extraction of heat from the stripper bottoms stream 34 in side reboilers 66, feed/effluent exchanger 64, and cross exchanger 60, additional heat may be recovered from the partially cooled stripper bottoms 70 in reboilers 20, which may include a bottoms reboiler and one or more side reboilers as further illustrated in FIG. 3, described below. Following extraction of heat in reboilers 20, a portion of the ethane stripper bottoms, which may include adsorbent-reactant and second adsorbent-reactant, may be withdrawn via flow line 36. Downstream of flow line 36, fresh or make-up adsorbent-reactant may be added via flow line 38, resulting in adsorbent-reactant feed stream 14. Feed stream 14 may be further cooled via one or more exchangers 72 to the desired absorber column inlet temperature, such as to about 10° C., for example.

In addition to the heat integration noted above, FIG. 2 additionally illustrates a condenser 80 on the overhead vapor stream 32 from the ethane stripper. Further, a heat exchanger 82 may be provided to chill a combined second absorbent feed stream 53 to the desired inlet temperature for each of streams 41, 51, for providing the appropriate operating temperature profile for each of scrubbers 40, 50.

Referring now to FIG. 3, a simplified process flow diagram of a reboiled absorber column according to embodiments herein is illustrated, where like numerals represent like parts. As described above, a vent gas 10, which may include methane, ethane, and ethylene, among other components, is fed to a reboiled vent absorber 12. In reboiled vent absorber 12, the vent gas is contacted in countercurrent flow with an adsorbent 14, producing a bottoms rich oil 18, including the absorbent, ethane and ethylene, and an overhead vapor stream 16, including the methane. The bottoms rich oil stream 18 is then fed to a reaction zone 24 for reaction of the ethylene to produce a desired end product, resulting in a lean oil stream 26 containing ethane and essentially no ethylene.

The separations in the reboiled absorber column are facilitated by a temperature differential and flow of absorbent favoring absorption of ethane and ethylene and rejection of methane. Reboiled absorber column 12 may include a reboiler 20, which may indirectly heat the column bottoms 300 using a heat exchange medium, such as hot water, steam, or oil. Additional heat may be input into the reboiled absorber column via one or more side reboilers 320. As illustrated, the system includes five side reboilers 320 (320A, 320B, 320C, 320D, and 320E).

The absorbent 34 is recycled from the ethane stripper (not illustrated), which is operating at a higher temperature than the desired inlet temperature of the absorbent 14 when it is introduced to the top of the reboiled absorber column. Thus, it is necessary to remove heat from the hot absorbent stream 34.

The hot absorbent stream 34 may be contacted in indirect heat exchange with reboiled absorber column bottoms 18 in exchanger 60, increasing the temperature of the bottoms 18 closer to that of the reaction zone 24 operating conditions, producing an absorbent stream 70 of reduced temperature. Further heat may be extracted from the absorbent stream 70 via side reboilers 320, where the heat is extracted serially via indirect heat exchange with a liquid or vapor draw from sequentially higher side draw trays 322 (322A, 322B, 322C, 322D, and 322E), which may be adjacent or non-adjacent trays. For simplicity, the flow of absorbent is illustrated using circles A, B, C, and D (to/from A, to/from B, etc.).

Extraction of heat from the absorbent stream 70 via side reboilers 320 may result in cooled absorbent stream 324. Following extraction of heat in side reboilers 320, a portion of the absorbent may be withdrawn via flow line 36. Downstream of flow line 36, fresh or make-up adsorbent may be added via flow line 38, resulting in feed stream 14. Feed stream 14 may be further chilled via one or more exchangers 72 to the desired absorber column 12 inlet temperature.

As noted above, additional heat may be recovered from ethane stripper bottoms using one or more side reboilers and a feed/effluent exchanger. Referring now to FIG. 4, a simplified process flow diagram of a reboiled ethane stripper according to embodiments herein is illustrated.

Ethane stripper 28 may include a reboiler 30, which may indirectly heat a portion of the column bottoms 400 using a heat exchange medium, such as hot water, steam, or oil. Additional heat may be input into the ethane stripper column via one or more side reboilers 66. As illustrated, the system includes two side reboilers 66A, 66B. A second bottoms portion 410 may be withdrawn from the ethane stripper 28. Heat may be extracted from the bottoms stream 410 via indirect heat exchange with a liquid or vapor draw from sequentially higher side draw trays 420 (420A, 420B), which may be adjacent or non-adjacent trays.

Extraction of heat from the ethane stripper bottoms 410 via side reboilers 66 may result in a partially cooled stripper bottoms stream 430. Partially cooled stripper bottoms 430 may then be used in feed/effluent exchanger 64 to provide additional heat to the reaction zone effluent 26 before introduction to the ethane stripper 28, and then fed via flow line 70 for further cooling before introduction of the adsorbent to reboiled absorber column 12, as described above with respect to FIGS. 2 and 3.

In addition to the heat integration described, FIG. 4 additionally illustrates an overhead system 435 on the overhead vapor stream from the ethane stripper 28. The ethane stripper overhead may be partially condensed in a condenser 80, which may be used to generate steam, for example, and then fed to an ethane stripper accumulator 437. Vapor from drum 437 may be further condensed in an ethane stripper trip condenser 439, which may be an air cooled condenser, prior to recovering ethane product stream 32.

Figure 5:
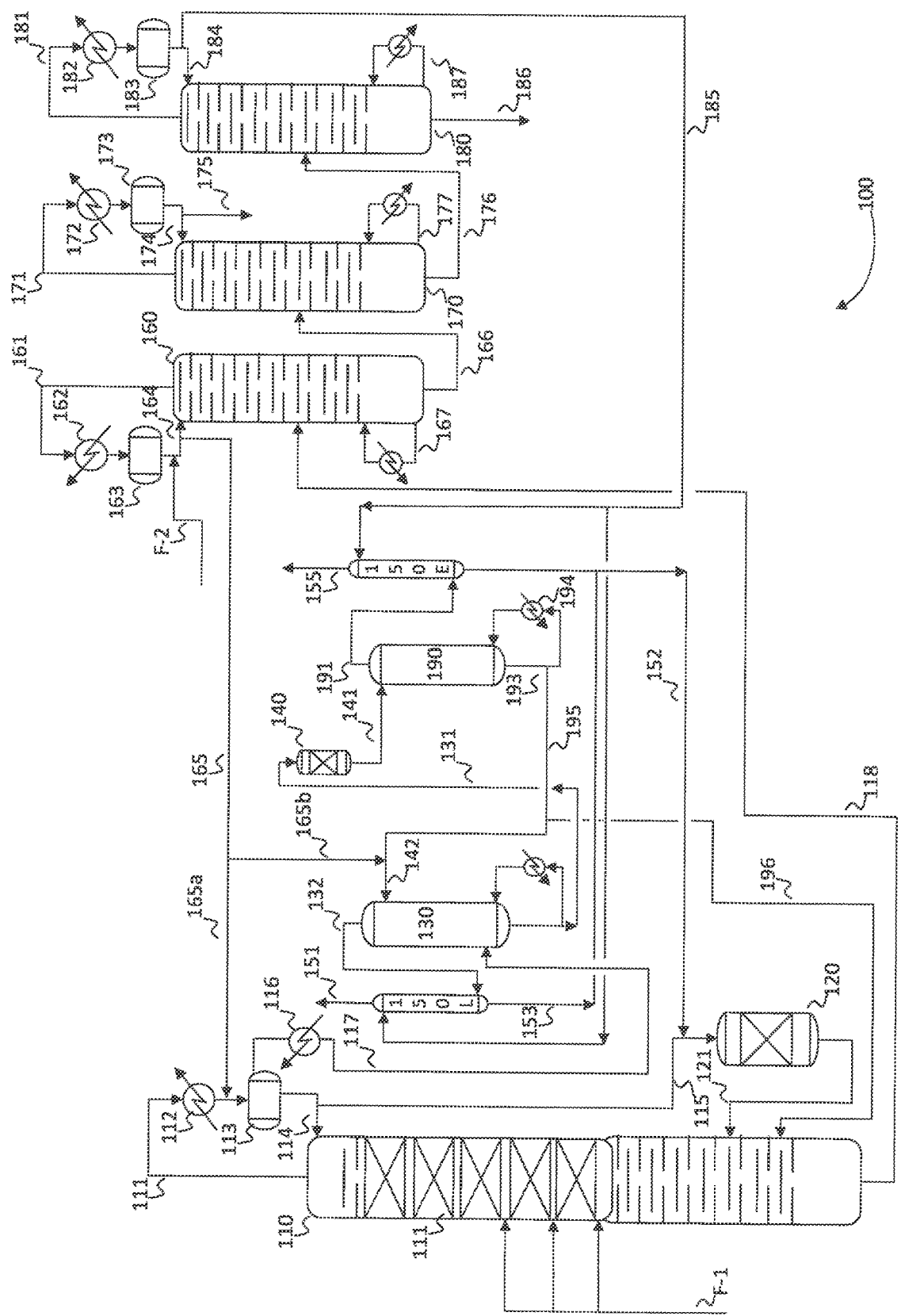
FIG. 5 is a simplified process flow diagram of a system for producing ethylbenzene incorporating ethane recovery systems disclosed herein.

The systems for ethane recovery disclosed herein may be used for recovery of ethane from an alkylation process vent gas system, for example. Referring now to FIG. 5, a simplified process flow diagram of a system for producing ethylbenzene incorporating ethane recovery systems disclosed herein is illustrated.

An ethylene feed F-1 and a benzene feed F-2 are introduced into the ethylbenzene production process 100 as shown. Ethylene feed F-1 can contain 5% to 100% by volume of ethylene, and can optionally be an offgas from a refinery operation such as FCC, which generally contains about 10% to about 30% by volume of ethylene. A typical FCC offgas contains 50% to 70% methane and hydrogen, with the balance being about equal amounts of ethane and ethylene and minor amounts of other hydrocarbon components. In some embodiments, feedstock F-1 contains 30% to 50% by volume of ethylene with the rest of the components including methane, ethane, hydrogen and other components. In other embodiments, the feed F-1 can be polymer grade ethylene.

Ethylene feed F-1 is fed to an alkylator 110, which in some embodiments is a catalytic distillation column including one or more reaction zones 111 containing a suitable alkylation catalyst, such as one or more catalyst selected from zeolite X, zeolite Y, zeolite L, TMA Offretite, mordenite, amorphous silica-alumina, zeolite BEA (beta), zeolite MWW, or MFI catalyst. The catalyst may be contained in packaged bales in some embodiments. Various types of catalytic distillation apparatus and methods and apparatus are known in the art. Alkylator 110 may be a mixed phase (liquid/vapor) reactor operating at alkylation reaction conditions, such as at a pressure of from about 270 psig to about 550 psig and a temperature of from about 185° C. to about 250° C., and a phenyl to ethyl ratio ranging from about 2.0 to about 3.5. Alkylator 110 may be configured to handle dilute ethylene feed and is capable of handling variations in the ethylene content and flow rate.

The feed F-1 may be injected at multiple points in the reactor and is contacted and dissolved in the liquid benzene introduced into the alkylator 110 via line 114 and flowing downward through the catalyst packing in the column 110. The ethylene absorbed by the benzene reacts with the benzene upon contact with the catalyst to form ethylbenzene and minor amounts of PEB.

The outflow of liquid from the bottom of the alkylator 110 (i.e., the ethylbenzene-containing liquid) is sent via line 118 to distillation column 160. Column 160 separates benzene from the ethylbenzene product and heavier components. The benzene is distilled overhead as a vapor and is sent via line 161 to condenser 162 where it is liquefied and held in accumulator 163. Benzene from accumulator 163 is sent via line 164 back to column 160 as a reflux. A portion 165 of the benzene is drawn off from line 164 and is sent via line 165a to the overhead from the alkylator 110, and via line 165b to the reboiled vent absorber 130. Fresh benzene feed F-2 may be introduced into line 164. Alternatively or additionally, the fresh benzene may be introduced to other places in the process that are benzene rich. The fresh benzene should be free of amines, aldehydes, ketones, and basic nitrogen compounds, which can poison the catalysts used in the process. Bottoms stream 167 is recirculated back to the column 160 through a reboiler.

Bottoms stream 166 containing ethylbenzene and PEB is sent to distillation column 170. Column 170 separates the ethylbenzene product from PEB. Bottom stream 177 is recirculated back to ethylbenzene column 170 through a reboiler. Bottom stream 176 containing PEB is sent to distillation column 180 for separation of PEB. The overhead ethylbenzene vapor stream 171 from column 170 is liquefied in condenser 172 and sent to accumulator 173. A portion of the overhead is returned to column 170 as reflux via line 174. Another portion is withdrawn via line 175 as ethylbenzene product.

Column 180 separates the PEB (e.g., diethyl benzene) from a heavy flux oil. The bottom stream 187 is recirculated back to column 180 through a reboiler. A portion of the bottoms is withdrawn via line 186 as a heavy flux oil. The flux oil may contain diphenylethane, tetraethylbenzene, and other high boiling components, and can be used as a heat transfer fluid, fuel oil or an absorbent. The overhead PEB vapor stream 181 is liquefied in condenser 182 and sent to accumulator 183. A portion of the overhead is returned to column 180 via line 184 as a reflux. Another portion of the PEB overhead is sent via line 185 to ethane vent scrubber 150E and lights vent scrubber 150L.

Considering once again the alkylator 110, the overhead vapor 111 from the alkylator contains unconverted olefin as well as ethane and one or more light components such as hydrogen, methane, carbon monoxide, carbon dioxide, propane and/or nitrogen, and is partially liquefied by condenser 112 and sent to accumulator 113. Also received into the accumulator 113 is a portion 165a of the benzene stream 165, which is divided into portions 165a and 165b as noted above. Accordingly, accumulator 113 contains combined recycled benzene and condensed alkylator overhead, as well as uncondensed vapor. A portion of the liquid from accumulator 113 is sent back to the alkylator 110 as reflux 114. Another portion is sent via line 115 to transalkylator 120. Transalkylator 120 also receives a stream of PEB from vent scrubbers 150E, 150L via line 152. In transalkylator 120, the benzene (from line 115) and the PEB (from line 152) react to form ethylbenzene, which is recycled back to alkylator 110 via line 121.

Transalkylator 120 may contain a suitable transalkylation catalyst, such as zeolite beta, zeolite Y or other suitable zeolite, and is operated under suitable transalkylation reaction conditions. Transalkylation reaction conditions may include, for example, a temperature of from 185° C. to about 250° C., a pressure of from about 350 psig to about 600 psig, a space velocity of from about 3.5 to 5.0 WHSV, and a molar ratio of phenyl to ethyl of from about 2.0 to about 5.0, wherein 3.0 is preferred.

The uncondensed vapor from accumulator drum 113 may contain ethylene, benzene and inerts such as ethane, methane and hydrogen, and may be sent via line 117 to reboiled vent absorber 130 for recovery of aromatics, ethane, and ethylene. Optionally, a vent condenser 116 may be used to further condense vapors exiting drum 113. The vapor stream flowing upward in reboiled vent absorber 130 is contacted with a downward flow of de-ethanized substantially olefin-free lean oil from line 142 containing benzene and ethylbenzene but substantially no ethylene. Reboiled vent absorber 130 can be a packed column or a tray column operating in countercurrent mode.

The de-ethanized lean oil may be operated to dissolve essentially all of the ethylene and ethane. The bottoms from the reboiled vent absorber 130, containing a rich oil (i.e., with dissolved ethylene and ethane), is sent via line 131 to a finishing reactor 140 for conversion of ethylene and benzene to ethylbenzene. The rich oil stream may contain, for example, at least 0.2% by weight of ethylene, such as at least about 0.3 wt % ethylene, at least about 0.4 wt % ethylene, at least about 5.0 wt % ethylbenzene, at least about 10 wt % ethylbenzene, or at least about 13 wt % ethylbenzene.

Finishing reactor 140 is a second alkylator, which may contain a fixed bed of loose catalyst, such as zeolite Y or, zeolite BEA (beta), zeolite MWW, Mordenite, or MFI catalyst and may operate adiabatically in a single, liquid phase. Alkylation in the liquid phase is efficient and requires less catalyst than alkylation in the mixed vapor/liquid phases. Conversion of ethylene in reactor 140 is substantially complete. Finishing reactor 140 may operate at a temperature of from about 200° C. to about 230° C., a pressure of from about 550 psig to about 900 psig, and a phenyl:ethyl mole ratio of from about 2.0 to about 10.0. The high phenyl:ethyl mole ratio results in excellent catalyst selectivity and stability.

The effluent stream 141 from the finishing reactor carries a lean oil containing benzene and ethylbenzene along with dissolved ethane. This lean oil is sent to de-ethanizer 190, which removes inert light components, such as ethane. The overhead 191 from the de-ethanizer is first sent through a condenser (not shown), with the liquefied portion being refluxed to the de-ethanizer column 190. The remaining vapor is then sent via flow line 191 to the ethane vent gas scrubber 150E, where the upflow of gas is contacted with downflow of PEB from the PEB column 180 to recover ethane product stream 155. Overhead 191 may contain ethane, traces of water, and benzene. Bottom stream 193 of the de-ethanizer is cycled through reboiler 194 and re-introduced into de-ethanizer column 190. Another portion 195 is drawn off the bottom of the de-ethanizer. The bottom effluent 195 from the de-ethanizer carries a de-ethanized lean oil containing benzene and ethyl-benzene. A portion of the de-ethanizer bottoms 195 is cycled back to the alkylator 110 via line 196 to maintain the liquid inventory in the absorber system, and may carry the net amount of ethylbenzene made in finishing reactor 140.

A portion 165b of the benzene from the overhead 165 of the benzene column is fed into the lean oil stream to maintain a desired benzene concentration in the stream, which provides the desired selectivity in the finishing reactor 140. The resulting stream 142 may be cooled against the effluent 131 from the vent absorber in a heat exchanger (not shown), and further chilled in a cooler (not shown) to a temperature ranging from about −10° C. to about 40° C., such as a temperature in the range from about 5° C. to about 15° C., whereupon it is fed to the top of the reboiled vent absorber 130.

The overhead vapor from the reboiled vent absorber 130 containing methane, hydrogen, traces of water, non-aromatics, and benzene, is carried by stream 132 to lights scrubber 150L for aromatic recovery, where the upflow of gas is contacted with downflow of PEB from the PEB column 180. The lights vent scrubber 150L may be operated to reject into the overhead gas (line 151) a small amount of $C_6$ non-aromatics and benzene as well as the inerts (hydrogen, methane). The scrubbed vent gas exits the vent scrubber 150 via line 151. The overall ethylene conversion of the process is about 99.9%. The bottoms 153 from the vent scrubber 150, containing PEB and other aromatics, is sent to the transalkylator 120 via line 152 for conversion of the PEB to ethylbenzene by transalkylation with benzene.

As alluded to above, manufacture of ethylbenzene using a catalytic distillation reaction system may involve the alkylation of benzene with ethylene to yield a mixture of alkylated benzenes and excess benzene. This mixture (the alkylator bottoms) is sent to a distillation section to recover the ethylbenzene, benzene, flux oil and PEB.

In the alkylation reaction zone, ethylbenzene may be produced by a zeolite-catalyzed alkylation of benzene with ethylene, where the ethylene may be provided as a dilute ethylene feedstock, including methane and ethane, among other components. The alkylation reactions take place at mild temperature. Higher poly-ethylated benzenes (PEBs) are also produced to a lesser extent. Most of the ethylene is reacted in the alkylator.

Throughout the catalyst run length, the majority of ethylene in the dilute ethylene stream is converted in the Alkylator. Essentially all the remaining ethylene is reacted in a finishing reactor. The alkylator may be tower packed with bales containing beta zeolite catalyst. The bales may be installed in the alkylator in the manner of structured packing. For example, there may be a number of beds/bales of catalyst, with ethylene feed injection below each bed or below one or more of the lowermost beds.

The heat of reaction is removed by vaporizing hydrocarbons, and the alkylation may occur nearly isothermally, at low temperature and low pressure. The ethylene fed to the reactor does not contact the catalyst directly, but is absorbed and reacted in the liquid phase. The low ethylene concentration at the catalyst surface almost eliminates the oligomerization of the ethylene. Oligomerization of ethylene produces precursors to the formation of ethylbenzene impurities and of heavy compounds. The absence of oligomerization results in a high purity ethylbenzene product, high process yield, and long, stable catalyst operation.

The finishing reactor may contain loose beta zeolite catalyst and may operate adiabatically in the liquid phase. Because it receives only a small portion of the ethylene fed to the unit, ethylene concentrations in this reactor are also very low, resulting again in high selectivity and a very low rate of catalyst deactivation. The combination of the alkylator and the finishing Reactor is designed to achieve 100% ethylene conversion over the entire catalyst cycle.

Ethylbenzene product, excess benzene and by-product PEBs from the alkylator and finishing reactor are recovered in the distillation area of the unit. A transalkylator may be utilized to convert recovered PEB to additional EB product. Recycle benzene including unreacted excess benzene and fresh benzene feed is recovered in a benzene column and fed to alkylator.

The alkylator has an upper section containing beds of catalyst and a lower section containing distillation trays. The two sections are separated by an internal head. The lower (distillation) section is reboiled by an alkylator reboiler, which may be a fired heater. The upper (reaction) section of the alkylator contains a continuous liquid phase, which is aerated by the upward flow of vapor. Vapor from the top of the lower section of the alkylator is fed below the bottom catalyst bed. Dilute ethylene is fed below one or more of the lowermost catalyst beds.

Additional vapor is generated in the alkylator by the exothermic heat of reaction of benzene with ethylene. The main reaction is the alkylation of benzene with ethylene to produce ethylbenzene. At start-of-run (SOR), typically over 90% of the ethylene is reacted in the alkylator. The overhead vapor from the alkylator is cooled in the alkylator condenser by generating steam and subsequently in an alkylator trim condenser by generating additional steam.

The partially condensed overhead from these exchangers is collected in the alkylator overhead drum. Benzene make-up to the drum is provided by blowdown from the finishing reactor loop. The liquid from this drum is refluxed to the alkylator and the vapor is sent to the vent absorber. The system is typically designed for an end-of-run (EOR) ethylene conversion of 80%. The alkylator bottoms pump sends net bottoms to the distillation trains of the unit and circulates hot alkylate to the alkylator reboiler, vent absorber reboiler, and ethane stripper reboiler.

Offgas absorption and finishing reactor vapor may be fed to a reboiled vent absorber where unreacted ethylene is absorbed into a lean oil stream, consisting of benzene and ethylbenzene, and subsequently reacted in the finishing reactor to achieve overall complete ethylene conversion. In addition to absorbing ethylene, the vent absorber serves to make the required separation between methane (light key component) and ethane (heavy key component) via extractive distillation. Side reboilers utilizing ethane stripper bottoms (hot lean solvent) provide most of the heat to the tower. A bottoms reboiler, utilizing hot alkylate circulation from the bottoms of the alkylator, may provide the balance of the heat input to the column. The overhead vapor is sent to the lights vent scrubber for benzene recovery. The lean solvent that has been cooled by process interchange in the side reboilers is further cooled against cooling water in a vent absorber cooler and then chilled in a vent absorber chiller (EA-2008).

Figure 6:
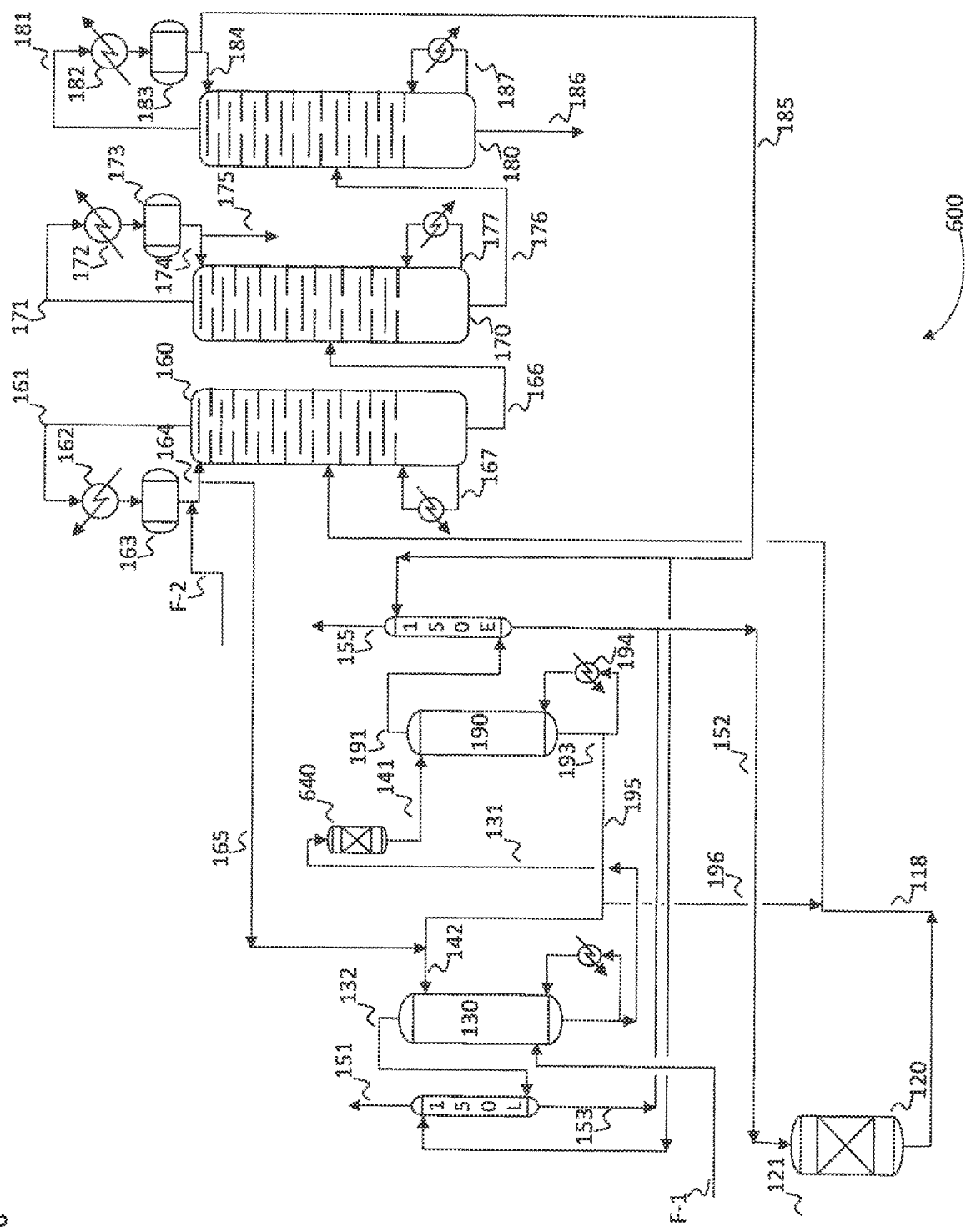
FIG. 6 is a simplified process flow diagram of a system for producing ethylbenzene incorporating ethane recovery systems disclosed herein.

The solvent circulation rate and the equipment sizes are based on the required absorption of ethane, since it is less soluble in benzene than ethylene. The carrying capacity of ethylene is significantly higher than utilized when the alkylator conversion is 80-90%. Therefore, the ethylene conversion in the alkylator can be significantly reduced and the absorption of ethylene from the alkylator vent gas can be significantly increased in order to reduce the size and cost of the alkylator system. The effect of lower alkylator conversion on the absorption system is minimal, and the increased size and cost of the liquid-phase finishing reactor is small compared with the cost savings in the alkylation system. At the extreme, the alkylation system can be entirely eliminated, as illustrated in FIG. 6 and described further below.

Rich oil, containing benzene, ethylbenzene, unconverted ethylene, ethane and a small amount of methane, is pumped and then heated against hot process liquid in the finishing reactor interchanger, before entering the finishing reactor. The finishing reactor effluent is then further heated in the ethane stripper feed/effluent exchanger by ethane stripper bottoms and fed to the top of the ethane stripper.

Ethylbenzene and poly-ethylated benzenes made in the finishing reactor are removed from the circulating loop by taking a blowdown from the partially cooled lean oil at a point downstream of the vent absorber side reboilers. The blowdown rate is set based on the benzene make-up requirements of the alkylator system. Benzene make-up to the finishing reactor loop is provided by a portion of the recycle benzene and fed to the loop downstream of where the blowdown is taken, before the vent absorber cooler.

The heated effluent from the finishing reactor enters the top of the ethane stripper. This column recovers ethane by-product in the net overhead, which may be used as a feed to an ethane cracker. The stripper bottoms is used as heating medium in the ethane stripper side reboilers, in the finishing reactor interchanger, and in the vent absorber reboilers before being cooled in the vent absorber cooler and chilled in the vent absorber chiller and used as lean solvent in the vent absorber. Hot alkylate circulation from the alkylator bottoms pump provides heat to the ethane stripper reboiler. Ethane stripper overhead vapor is partially condensed in the ethane stripper main condenser, which generates steam, and sent to ethane stripper accumulator. The liquid from this drum is pumped and sent back to the stripper as reflux. Vapor from this drum is further condensed in the ethane stripper trim condenser, an air cooled condenser. Condensed liquid from this exchanger is sent back to the overhead drum while the ethane vapor is further cooled against cooling water in the ethane vent scrubber feed cooler before being fed to the ethane vent scrubber.

In the lights vent scrubber, the vent gas is contacted with a cold PEB stream, recycled from the distillation section of the unit. Hydrogen, methane and a small amount of ethane are taken overhead and sent to the fuel gas header. A portion of this stream could be considered for use as regeneration gas for treaters on an intermittent basis. Aromatics are scrubbed from the column feed and sent back for recovery in order to maximize yield.

In the ethane vent scrubber, the ethane is also contacted with a cold PEB stream, recycled from the distillation section of the unit. Ethane product is taken overhead. Aromatics are scrubbed from the column feed and sent back for recovery in order to maximize yield. A slip stream from the PEB recycle may be first cooled in a PEB cooler and then chilled in a PEB chiller. The chilled PEB may then be used as absorbent in the two vent gas scrubbers.

As noted above, systems according to embodiments herein may allow elimination of the alkylator altogether. Referring now to FIG. 6, a simplified process flow diagram of a system for the production of ethylbenzene is illustrated, where like numerals represent like parts.

An ethylene feed F-1 and a benzene feed F-2 are introduced into the ethylbenzene production process 600 as shown. Ethylene feed F-1 can contain 5% to 100% by volume of ethylene, and can optionally be an offgas from a refinery operation such as FCC, which generally contains about 10% to about 30% by volume of ethylene. A typical FCC offgas contains 50% to 70% methane and hydrogen, with the balance being about equal amounts of ethane and ethylene and minor amounts of other hydrocarbon components. In some embodiments, feedstock F-1 contains 30% to 50% by volume of ethylene with the rest of the components including methane, ethane, hydrogen and other components. In other embodiments, the feed F-1 can be polymer grade ethylene.

Benzene Feed F-2 is processed in a manner similar to the embodiment illustrated and described with respect to FIG. 5. Column 160 separates benzene from the ethylbenzene product and heavier components. The benzene is distilled overhead as a vapor and is sent via line 161 to condenser 162 where it is liquefied and held in accumulator 163. Benzene from accumulator 163 is sent via line 164 back to column 160 as a reflux. A portion 165 of the benzene is drawn off from line 164 and is sent via line 165 to the reboiled vent absorber 130. Fresh benzene feed F-2 may be introduced into line 164. Alternatively or additionally, the fresh benzene may be introduced to other places in the process that are benzene rich. The fresh benzene should be free of amines, aldehydes, ketones, and basic nitrogen compounds, which can poison the catalysts used in the process. Bottoms stream 167 is recirculated back to the column 160 through a reboiler.

Bottoms stream 166 containing ethylbenzene and PEB is sent to distillation column 170. Column 170 separates the ethylbenzene product from PEB. Bottom stream 177 is recirculated back to ethylbenzene column 170 through a reboiler. Bottom stream 176 containing PEB is sent to distillation column 180 for separation of PEB. The overhead ethylbenzene vapor stream 171 from column 170 is liquefied in condenser 172 and sent to accumulator 173. A portion of the overhead is returned to column 170 as reflux via line 174. Another portion is withdrawn via line 175 as ethylbenzene product.

Column 180 separates the PEB (e.g., diethyl benzene) from a heavy flux oil. The bottom stream 187 is recirculated back to column 180 through a reboiler. A portion of the bottoms is withdrawn via line 186 as a heavy flux oil. The flux oil may contain diphenylethane, tetraethylbenzene, and other high boiling components, and can be used as a heat transfer fluid, fuel oil or an absorbent. The overhead PEB vapor stream 181 is liquefied in condenser 182 and sent to accumulator 183. A portion of the overhead is returned to column 180 via line 184 as a reflux. Another portion of the PEB overhead is sent via line 185 to ethane vent scrubber 150E and lights vent scrubber 150L.

Transalkylator 120 receives a stream of PEB from vent scrubbers 150E, 150L via line 152. In transalkylator 120, the benzene and the PEB react to form ethylbenzene, which is forwarded to the distillation train (160, 170, 180) for separation as described above.

In this embodiment, ethylene feed F-1 is fed to reboiled vent absorber 130. The feed vapors flowing upward in reboiled vent absorber 130 are contacted with a downward flow of de-ethanized substantially olefin-free lean oil from line 142 containing benzene and ethylbenzene but substantially no ethylene. Reboiled vent absorber 130 can be a packed column or a tray column operating in countercurrent mode.

The de-ethanized lean oil may be operated to dissolve essentially all of the ethylene and ethane. The bottoms from the reboiled vent absorber 130, containing a rich oil (i.e., with dissolved ethylene and ethane), is sent via line 131 to alkylation reactor 640 for conversion of ethylene and benzene to ethylbenzene. The rich oil stream may contain, for example, at least 0.2% by weight of ethylene, such as at least about 0.3 wt % ethylene, at least about 0.4 wt % ethylene, at least about 5.0 wt % ethylbenzene, at least about 10 wt % ethylbenzene, or at least about 13 wt % ethylbenzene.

Alkylation reactor 640 may contain a fixed bed of catalyst, such as zeolite Y or, zeolite BEA (beta), zeolite MWW, Mordenite, or MFI catalyst and may operate adiabatically in a single, liquid phase, for example. Conversion of ethylene in alkylation reactor 640 may be substantially complete. Alkylation reactor 640 may operate at a temperature of from about 200° C. to about 230° C., a pressure of from about 550 psig to about 900 psig, and a phenyl:ethyl mole ratio of from about 2.0 to about 10.0. The high phenyl:ethyl mole ratio results in excellent catalyst selectivity and stability.

The effluent stream 141 from the alkylation reactor carries a lean oil containing benzene and ethylbenzene along with dissolved ethane. This lean oil is sent to de-ethanizer 190, which removes inert light components, such as ethane. The overhead 191 from the de-ethanizer is first sent through a condenser (not shown), with the liquefied portion being refluxed to the de-ethanizer column 190. The remaining vapor is then sent via flow line 191 to the ethane vent gas scrubber 150E, where the upflow of gas is contacted with downflow of PEB from the PEB column 180 to recover ethane product stream 155. Overhead 191 may contain ethane, traces of water, and benzene. Bottom stream 193 of the de-ethanizer is cycled through reboiler 194 and re-introduced into de-ethanizer column 190. Another portion 195 is drawn off the bottom of the de-ethanizer. The bottom effluent 195 from the de-ethanizer carries a de-ethanized lean oil containing benzene and ethyl-benzene. A portion of the de-ethanizer bottoms 196, which may carry the net amount of ethylbenzene made in alkylation reactor 640, may be combined with transalkylation reactor 120 effluent 118 and forwarded to separator 160.

Overhead 165 of the benzene column is fed into the lean oil stream to maintain a desired benzene concentration in the stream, which provides the desired selectivity in the alkylation reactor 640. The resulting stream 142 may be cooled against the effluent 131 from the vent absorber in a heat exchanger (not shown), and further chilled in a cooler (not shown) to a temperature ranging from about −10° C. to about 40° C., such as a temperature in the range from about 5° C. to about 15° C., whereupon it is fed to the top of the reboiled vent absorber 130.

The overhead vapor from the reboiled vent absorber 130 containing methane, hydrogen, traces of water, non-aromatics, and benzene, is carried by stream 132 to lights scrubber 150L for aromatic recovery, where the upflow of gas is contacted with downflow of PEB from the PEB column 180. The lights vent scrubber 150L may be operated to reject into the overhead gas (line 151) a small amount of $C_6$ non-aromatics and benzene as well as the inerts (hydrogen, methane). The scrubbed vent gas exits the vent scrubber 150 via line 151. The overall ethylene conversion of the process is about 99.9%. The bottoms 153 from the vent scrubber 150, containing PEB and other aromatics, is sent to the transalkylator 120 via line 152 for conversion of the PEB to ethylbenzene by transalkylation with benzene.

As described above, embodiments herein provide for efficient processes and systems for the recovery of ethane from a vapor stream containing methane, ethane and ethylene. Systems described herein can be used to absorb all of the ethylene and ethane contained in FCC, RFCC and VGO offgases and to produce a mixed ethylene/ethane stream and a mixed lights (methane and hydrogen) stream. Such systems can be used for the absorption of ethylene and ethane contained in FCC, RFCC and VGO offgases and to separate the ethylene and ethane from methane, hydrogen and other lights contained in offgas feed for use in any process where ethylene is required and ethane can be fed to an ethylene unit.

For example, embodiments disclosed herein may be used to recover a high purity ethane stream from a vent gas of an alkylation process using a dilute ethylene feed. The ethane recovery systems disclosed can be used in conjunction with a CDTECH EB unit, available from Lummus Technology, Inc., Woodlands, Tex., and containing a catalytic distillation (CD) Alkylator and a finishing reactor, for the conversion of ethylene to ethylbenzene. The relative conversion of ethylene in the CD alkylator and finishing reactor can be adjusted based on feed gas composition to produce an optimal design.

Advantageously, embodiments disclosed herein may allow the use of fluid catalytic cracker (FCC) offgas, residue fluid catalytic cracker (RFCC) offgas, and vacuum gas oil (VGO) cracking offgas in an alkylation unit. Embodiments disclosed herein may also allow near full recovery of ethane from the vent gas, which may be fed to an ethane cracker in order to produce additional ethylene and improve plant economics.

As the required solvent circulation for recovery of the ethane is based on the required ethane absorption, the conversion of ethylene in the alkylator may advantageously be reduced to a point where the ethylene absorption requirement equals the ethane absorption requirement. This may advantageously allow operation of an alkylation reactor, such as a catalytic distillation alkylation reactor, to operate at very low CD alkylator ethylene conversions, additionally allowing a reduction in the required amount of catalyst in the alkylation reactor. Additionally, embodiments herein may allow for production of ethylbenzene from FCC, RFCC, and VGO cracking offgas with only a fixed-bed, liquid phase alkylator.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the recovery of ethane, comprising:
   feeding a first stream comprising methane, ethane, and ethylene to a reboiled absorber column;
   contacting the first stream with an absorbent-reactant in the reboiled absorber column to absorb essentially all of the ethane and ethylene, producing a rich oil bottoms stream comprising the absorbent-reactant, ethylene, and ethane, and a vapor stream comprising methane, wherein the contacting is performed operating the reboiled absorber column at a bottoms temperature in the range from about 150° C. to about 220° C. and an overhead pressure in the range from about 200 psig to about 500 psig;
   reacting the ethylene and the absorbent-reactant in a reaction zone, producing a reaction zone effluent comprising ethane and a reaction product;
   stripping the effluent in a stripper to produce a lean oil bottoms stream and an overhead vapor stream consisting essentially of ethane and including essentially no ethylene, methane, and hydrogen;
   wherein the reboiled absorber column comprises multiple reboilers configured to sequentially extract heat from the lean oil bottoms stream from the stripper;
   extracting heat from the lean oil bottoms stream from the stripper via one or more stripper side reboilers.

2. The process of claim 1, wherein the first stream and the vapor stream each further comprise one or more of nitrogen, hydrogen, carbon monoxide, and carbon dioxide.

3. The process of claim 1, further comprising:
   operating the stripper at a bottoms temperature in the range from about 200° C. to about 280° C.

4. The process of claim 1, further comprising recycling at least a portion of the lean oil bottoms stream from the stripper to the reboiled absorber column as the absorbent-reactant.

5. The process of claim 4, further comprising introducing the absorbent-reactant proximate an upper end of the reboiled absorber column at a temperature in the range from about −20° C. to about 50° C.

6. The process of claim 1, further comprising contacting the lean oil bottoms stream in indirect heat exchange with the reaction zone effluent and/or the rich oil bottoms stream.

7. The process of claim 6, further comprising withdrawing a portion of the lean oil stream intermediate the contacting in indirect heat exchange and introduction of a remaining portion of the lean oil stream to the reboiled absorber column.

8. The process of claim 7, further comprising admixing fresh and/or make-up adsorbent-reactant with the remaining portion of the lean oil stream.

9. The process of claim 1, further comprising feeding the overhead vapor stream comprising ethane to a cracker.

10. A process for the recovery of ethane, comprising:
feeding a first stream comprising methane, ethane, and ethylene to a reboiled absorber column;
contacting the first stream with an absorbent-reactant in the reboiled absorber column to absorb essentially all of the ethane, producing a rich oil stream comprising the absorbent-reactant, ethylene, and ethane, and a vapor stream comprising methane, where the contacting is performed operating the reboiled absorber column at a bottoms temperature in the range from about 150° C. to about 220° C. and an overhead pressure in the range from about 200 psig to about 500 psig;
reacting the ethylene and the absorbent-reactant in a reaction zone, producing an effluent comprising ethane and a reaction product;
stripping the effluent in a stripper to produce a lean oil bottoms stream and an overhead vapor stream consisting of ethane and any entrained absorbent-reactant and reaction product, and wherein the overhead vapor stream includes essentially no ethylene, methane, and hydrogen;
contacting the overhead vapor stream with a first portion of a second absorbent-reactant in a first scrubber to absorb the entrained absorbent-reactant and reaction product in the overhead vapor stream and to produce a first scrubber bottoms stream comprising the second absorbent-reactant and a first scrubber overhead stream consisting essentially of ethane;
contacting the vapor stream comprising methane with a second portion of the second absorbent-reactant in a second scrubber to absorb ethane, ethylene, and/or absorbent-reactant present in the vapor stream and to produce a second scrubber bottoms stream comprising the second absorbent-reactant and a second scrubber overhead stream comprising methane;
wherein the reboiled absorber column comprises multiple reboilers configured to sequentially extract heat from the lean oil bottoms stream from the stripper;
extracting heat from the lean oil bottoms stream from the stripper via one or more stripper side reboilers.

11. The process of claim 10, wherein the absorbent-reactant comprises benzene, the second absorbent-reactant comprises poly-ethylated benzenes, and the reaction product comprises ethylbenzene.

12. The process of claim 10, wherein the first stream and the vapor stream each further comprise nitrogen and/or hydrogen.

13. The process of claim 10, further comprising:
operating the stripper at a pressure in the range from about 100 psig to about 450 psig.

14. The process of claim 10, further comprising recycling at least a portion of the lean oil bottoms steam from the stripper to the reboiled absorber column as the absorbent-reactant, wherein the absorbent-reactant in introduced to the reboiled absorber column at a temperature in the range from about −20° C. to about 50° C.

* * * * *